(12) United States Patent
Maktura

(10) Patent No.: US 8,749,252 B2
(45) Date of Patent: Jun. 10, 2014

(54) METHOD AND EQUIPMENT FOR MONITORING THE CURRENT DRAINED BY THE GROUNDING ELECTRODE IN ELECTRIC IMPEDANCE TOMOGRAPHY

(75) Inventor: Edward Lazo Maktura, São Paulo (BR)

(73) Assignee: Timpel S.A., Sao Paulo (BR)

( * ) Notice: Subject to any disclaimer, the term of this patent is extended or adjusted under 35 U.S.C. 154(b) by 749 days.

(21) Appl. No.: 12/995,350

(22) PCT Filed: Jun. 1, 2009

(86) PCT No.: PCT/BR2009/000147
§ 371 (c)(1),
(2), (4) Date: Mar. 4, 2011

(87) PCT Pub. No.: WO2009/146516
PCT Pub. Date: Dec. 10, 2009

(65) Prior Publication Data
US 2011/0148443 A1    Jun. 23, 2011

(30) Foreign Application Priority Data

Jun. 2, 2008 (BR) .................................... 0801684

(51) Int. Cl.
*G01R 27/08* (2006.01)
(52) U.S. Cl.
USPC .......................................... 324/705; 324/713
(58) Field of Classification Search
USPC ............. 324/705, 691, 649, 600, 76.11, 120, 324/522, 525, 713; 702/64, 57, 1
See application file for complete search history.

(56) References Cited

U.S. PATENT DOCUMENTS

| 4,200,108 A * | 4/1980 | Weigert ........................... 607/64 |
| 4,262,191 A * | 4/1981 | Lepper et al. ................. 219/497 |
| 5,544,662 A | 8/1996 | Saulnier et al. |
| 6,295,468 B1 | 9/2001 | Hess |
| 8,195,282 B2 * | 6/2012 | Hashimshony ............... 600/547 |
| 2007/0010758 A1 | 1/2007 | Matthiessen et al. |
| 2008/0001608 A1 | 1/2008 | Saulnier et al. |
| 2008/0097712 A1 | 4/2008 | Bruce et al. |
| 2012/0226333 A1 * | 9/2012 | Szeles ............................. 607/59 |

FOREIGN PATENT DOCUMENTS

EP    0747005 A    11/1996

* cited by examiner

*Primary Examiner* — Hoai-An D Nguyen
(74) *Attorney, Agent, or Firm* — TraskBritt

(57) ABSTRACT

There are disclosed a method and an equipment for monitoring current drained by a grounding electrode in an electric impedance tomography system. The grounding electrode and a set of electrodes may be simultaneously applied to a patient in an electric impedance tomography apparatus. The equipment may be configured to convert current into a voltage signal and amplify, demodulate, and filter the voltage signal in order to recover its almost continuous component. The equipment may further be configured to compare the value of the continuous component with limit/threshold values proportional to an intensity of an excitation current applied to the set of electrodes. In addition to detecting the disconnection of the grounding electrode, the comparison may also detect the disconnection of one or more tomography electrodes, as well as unbalance in the currents injected through the electrodes and the contact of the patient with voltage sources or conductive bodies.

21 Claims, 3 Drawing Sheets

METHOD AND EQUIPMENT FOR MONITORING THE CURRENT DRAINED BY THE GROUNDING ELECTRODE IN ELECTRIC IMPEDANCE TOMOGRAPHY

CROSS-REFERENCE TO RELATED APPLICATIONS

This application is a 35 U.S.C. 371 national phase application of PCT/BR2009/000147 entitled "Method and Equipment for Monitoring the Current Drained by the Grounding Electrode in Electric Impedance Tomography," filed Jun. 1, 2009, which claims the priority benefit of BR Patent Application No. PI0801684-4, filed Jun. 2, 2008, the entire disclosures of which are incorporated herein in their entirety.

FIELD OF THE INVENTION

The present invention relates to the detection of abnormal conditions of operation in electric impedance tomography systems, and refers more particularly to such conditions when associated with the grounding electrode.

DESCRIPTION OF THE PRIOR ART

Electric impedance tomography is a widely known and used technique, and consists in the positioning of a plurality of electrodes on a region of the patient, the injection of electric excitation signals between at least two of these electrodes, with simultaneous detection of the signals induced in the other electrodes and the processing of these signals in order to generate a plot indicative of the impedance in the tested region. At each measurement cycle the electrodes are set out in sequence such as to include all the electrodes installed on the patient, there being typically used systems with 32 electrodes.

These electrodes operate in differential mode, both in the cited current injection and in the operation of detection of the voltages. In order to avoid oscillations of the level of the detected signals, which would jeopardize the reconstitution of the tomography images, it is necessary to connect to the patient a floating ground electrode which function consists in draining eventual currents due to unbalance between electrodes, as well as those occurring when other equipment is used in the patient, such as an electric scalpel, and further, those caused by the contact of the patient with a conductive body (for example, the hospital bed, the side table, and other metallic utensils). That electrode should be connected away from the readout and injection electrodes in order to generate a uniform distribution of the floating ground in relation to the remaining electrodes. Such electrode is usually installed on the right or left leg region of the patient.

The disconnection of this electrode, when not detected and corrected, might generate distortions in the reconstruction of the image to be presented by the tomography equipment, and might induce errors in the interpretation of the images.

OBJECTS OF THE INVENTION

In light of what has been set forth heretofore, a first object of the invention consists in the provision of a detector capable of indicating the disconnection of the grounding electrode in an electric impedance tomography system.

One other object of the invention consists in the provision of a detector that might indicate an abnormal drainage of current caused by the use of another equipment or by the occasional contact of the patient with electrically conducting objects.

Another object of the invention consists in the provision of a detector capable of indicating the existence of an unbalanced condition in the injection of currents due to an internal imbalance of the current source of the tomography apparatus or caused by the disconnection of one or more electrodes used to inject current or to read out voltages.

BRIEF DESCRIPTION OF THE INVENTION

The cited objects, as well as others, are achieved by the present invention by means of the provision of an equipment that provides the detection of a signal corresponding to the value of the current drained through the grounding electrode as well as the treatment of this signal, subsequently conveying the same to be analyzed by means of an adequate software.

According to another characteristic of the invention, said equipment comprises means of protection against surges due to the use of a defibrillator, means for signal amplification, means for demodulation and means for analog-digital conversion of the amplified signal. Advantageously, the demodulation is carried out together with filtering that eliminates the high-frequency component of the detected signal, such component being in the range of 30 kHz to 300 kHz, as well as low-frequency oscillations above 0.5 Hz, producing as a result an almost continuous voltage.

According to another characteristic of the invention, the signal is detected in the form of a voltage measured by means of a low value resistor connected in series with the said grounding electrode.

According to still another characteristic of the invention, the proposed equipment allows the detection of eventual imbalances in the currents injected by the electrodes of the tomography apparatus, such as those caused by the disconnection of one such electrode.

According to a further characteristic of the invention, the proposed equipment allows the detection of the disconnection of the ground current drainage electrode.

According to yet another characteristic of the invention, the detection of the conditions of the drainage electrode comprises the comparison of the value of almost continuous voltage with maximum and minimum patterns.

DESCRIPTION OF THE FIGURES

The remaining characteristics and advantages of the invention will become more apparent from the description of a preferred embodiment of the invention, given for mere exemplificative purposes, and of the figures referring thereto, wherein.

DETAILED DESCRIPTION OF THE INVENTION

Figure 1:
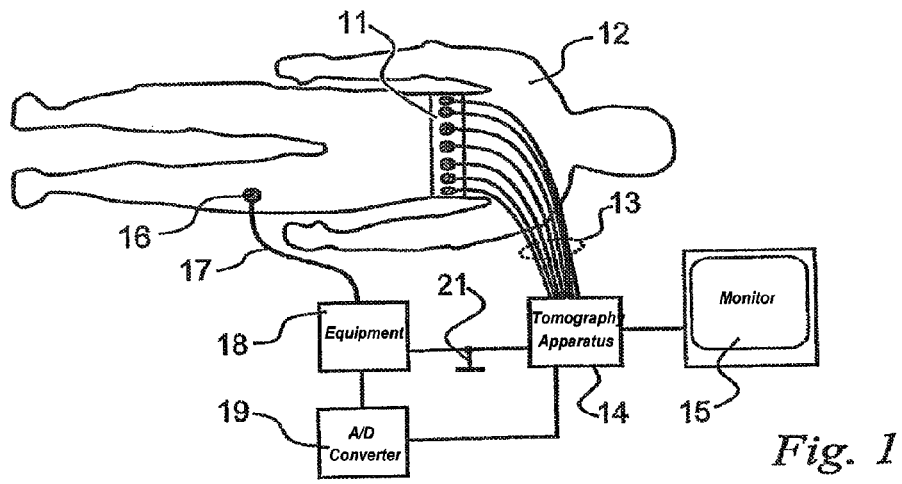
FIG. 1 illustrates the arrangement of the elements in an electric impedance tomography system and the relationship thereof with the equipment of the present invention.

According to what is illustrated in FIG. 1, an arrangement used for capturing tomography images by electric impedance comprises a set of electrodes normally provided on tomography electrodes 11 around a region of the body of a patient 12, connected by means of cables 13 to a tomography apparatus 14, which generates the image displayed on a monitor 15. A grounding electrode 16 is in contact with the thigh region of the patient 12 and is sufficiently removed from the electrodes used in the tomography to generate a substantially uniform distribution of the ground currents. The electrode 16 is connected, by means of a shielded cable 17, to equipment 18 that processes the signal by means of the circuit depicted in FIGS. 2 and 3, whereby the processed signal is conveyed to the digitizing and analysis device for checking of eventual anomalies. The equipment 18 and the tomography apparatus 14 are interconnected and are connected to the ground of system 21.

Figure 2:
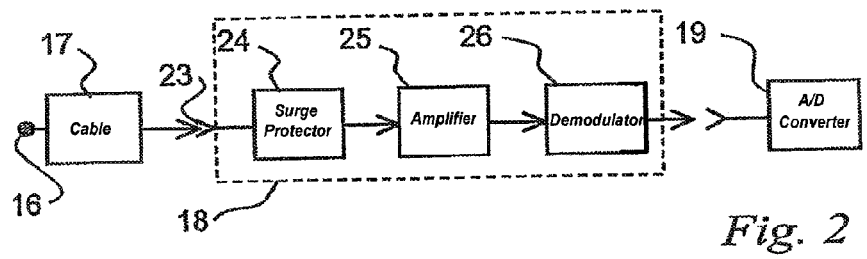
FIG. 2 is a block diagram illustration of the equipment proposed by the present invention.

According to the block diagram of FIG. 2, the object of the invention comprises the shielded cable 17 to which distal end is connected the grounding terminal 16, the proximal end of shielded cable 17 being connected to an input 23 of the equipment 18, in which first stage 24 consists in the means of protection against surges of voltage used in the defibrillator. Sequentially, the equipment 18 comprises a ground-draining current amplifier 25, which output is connected to a demodulator 26, provided with a low-pass filter set with a cut-off frequency setting of 0.5 Hz, which produces a substantially continuous voltage that is conveyed to a block 19 that may be integrated to the equipment that constitutes the object of the present invention or may constitute a separate unit. The block 19 digitizes the signal by means of A/D conversion and analyzes the result, comparing the characteristics of this signal with previously established patterns, such as to detect eventual anomalies, and if required, to activate the corresponding alarms.

Figure 3:
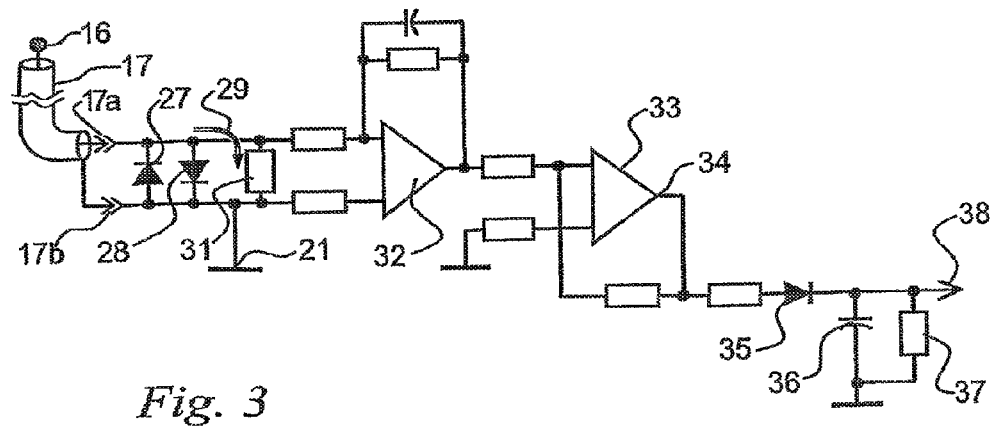
FIG. 3 illustrates a simplified schematic diagram of the components used in the equipment according to the present invention.

FIG. 3 shows, in a more detailed fashion, the schematic circuit of blocks 24, 25 and 26. For better clarity, there have been omitted in this figure the details relative to the supply of the circuit. As already mentioned, a ground drainage current 29 captured by the electrode 16 is fed into the equipment through the shielded cable 17 which web is grounded to avoid induction arising from external field sources. The protection against high voltage values, such as those arising from the use of external equipment like, for example, an electric scalpel or a defibrillator, is provided by fast-reacting diodes 27 and 28, connected in counter-parallel fashion between input terminals 17a and 17b, which divert the over-voltages to ground.

Figure 4:
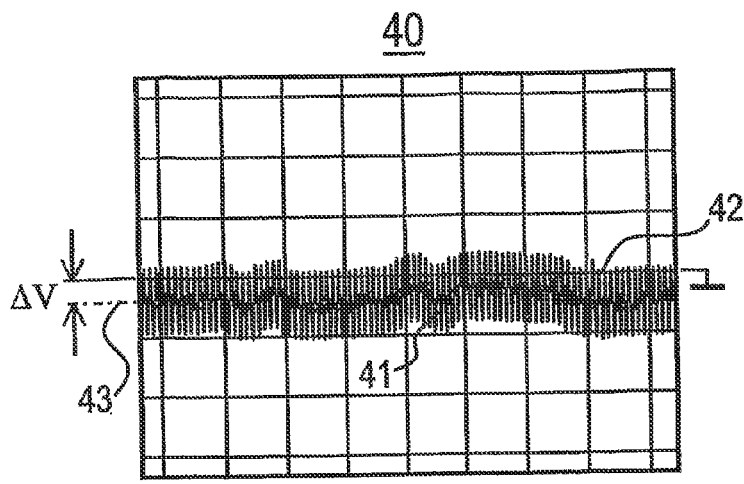
FIG. 4 illustrates the screen of an oscilloscope, showing the signal detected by the resistor connected in series with the grounding electrode.

In normal operating conditions, the ground drainage current 29, captured by the electrode 16 and introduced into the equipment through the cable 17, flows to ground through a resistor 31. The resistance of the resistor 31 should be sufficiently weak/low to avoid hindering the flow of this current. Values between 20Ω and 3000Ω are adequate for this function, there being preferably adopted a value around 100Ω. The signal resulting from the passage of this current by the resistor 31 has an alternate component, with the same frequency of the signal used for injecting the current into the tomography electrodes, superimposed on a direct current. This signal is introduced into the amplifier arrangement formed by operational amplifiers 32 and 33, which amplify the signal between 10 and 1000 times, where such amplification factor is preferably situated between 300 and 400 times. FIG. 4 represents the trace on a screen 40 of an oscilloscope showing the signal obtained at output pin 34 of the second operational amplifier 33, the signal presenting an alternate component 41 superimposed on a continuous voltage 43. This continuous component presents an offset $\Delta V$ with relation to ground potential 42. The signal is then rectified by a diode 35 and is filtered by a capacitor arrangement 36 together with a resistor 37, there resulting at an output terminal 38 an almost continuous voltage.

Figure 5:
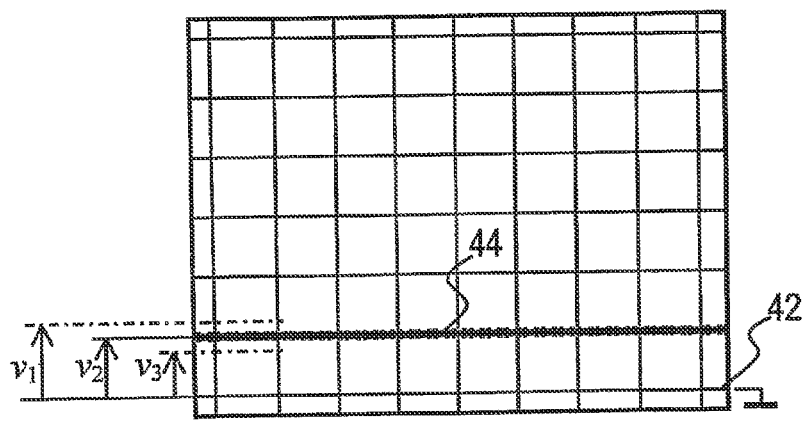
FIGS. 5 and 6 illustrate the images displayed on the screen of an oscilloscope, corresponding to the signal present at the terminal, when the grounding electrode is connected, for two different values of the excitation current applied to the electrodes of the tomography system.

When the system is operating normally, this almost continuous voltage is different from zero, and this difference is proportional to the excitation current of the tomography electrodes 11 (FIG. 1). In the trace of FIG. 5, it is noted that in the case that this current is equal to 3 mA, the signal taken at the output terminal 38 is presented as an almost continuous voltage 44, with a difference v2 relative to the zero axis 42, which corresponds to the ground potential in that figure. Still according to what is shown in the figure, the value of v2 is in a range comprised between the minimum v3 and the maximum v1. These values are stored in the memory of the analysis block 19, which is informed by the tomography equipment 14 on the current that is being employed for exciting the tomography electrodes 11, since this current defines the minimum limit v3 and the maximum limit v1 of the range of tolerance. Based on the cited data, the block 19 checks whether the voltage effectively measured at terminal 38 is within the tolerance limits, driving an alarm means or equivalent resource if this does not occur.

The presence of v2 results for the imbalance of the entire system when in normal operation, when there occurs a current leak to ground. Therefore, the presence of such imbalance indicates that the tomography images obtained are reliable. On the contrary, the absence of a drained current corresponds to an abnormal operation, resulting in a jeopardized image due to a significant increase of the noise level.

Figure 6:
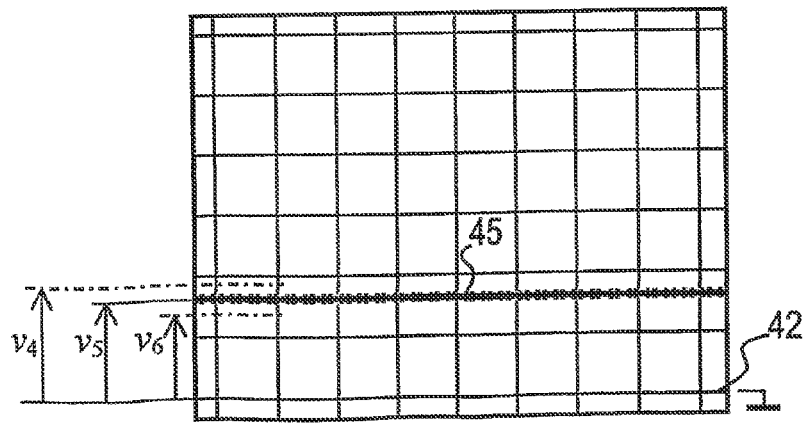

The difference between the voltage captured at the terminal 38 and the zero axis is proportional to the value of the excitation current applied to the tomography electrodes 11. In FIG. 6 there is depicted the trace on the oscilloscope screen when this current is increased to 5 mA. In this case, observed signal 45 has a value v5 relative to the zero axis 42, and this value, compared with v2 of the previous figure appears superior thereto in a relationship approximately equal to that of the excitation currents used, that is, 5/3. The limits of the tolerance range, indicated in FIG. 6 by the minimum value v6 and the maximum value v4 shall be proportionally increased, from the information provided by the tomography apparatus 14. Also in this case, the observed trace indicates that the voltage is within the limits of the referenced range, and therefore the grounding electrode 16 is correctly connected to the patient.

Figure 7:
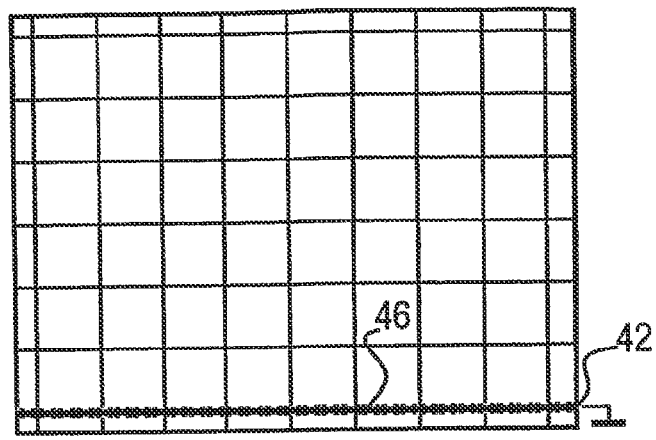
FIG. 7 illustrates the image on the screen of an oscilloscope, corresponding to the signal present at the output terminal of the circuit of FIG. 3, when the grounding electrode is disconnected.

Should voltage 46 shown in terminal 38 be equal to zero, as illustrated in the trace of FIG. 7, this will mean that the grounding electrode 16 is disconnected. Such disconnection might arise from an oversight of the operator or from the movement of the body of the patient himself or herself. In both cases, the analysis performed by the block 19 will detect this abnormal condition, and if necessary, will drive an alarm device.

Figure 8:
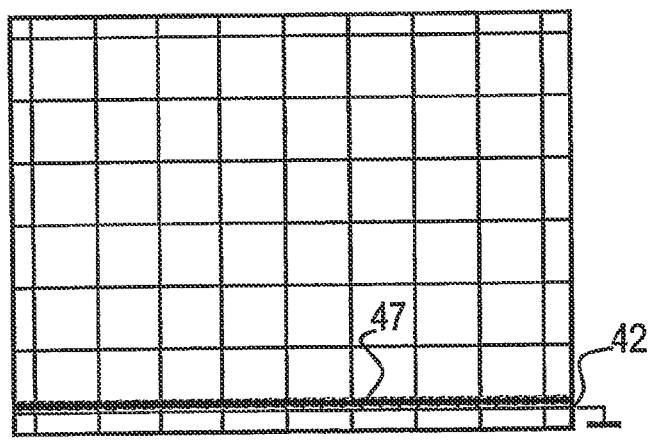
FIG. 8 illustrates the image on the screen of an oscilloscope when displaying the signal present at the output of the circuit of FIG. 3, when the grounding electrode is connected but there is no injection of current into the electrodes of the tomography apparatus.

In FIG. 8 there is illustrated the case where the electrode 16 is duly connected to the patient, but there is not being injected current into the tomography electrodes 11. As may be observed, in such condition a signal 47 is not exactly equal to zero, and exhibits a slight offset with relation to the zero axis 42.

Figure 9:
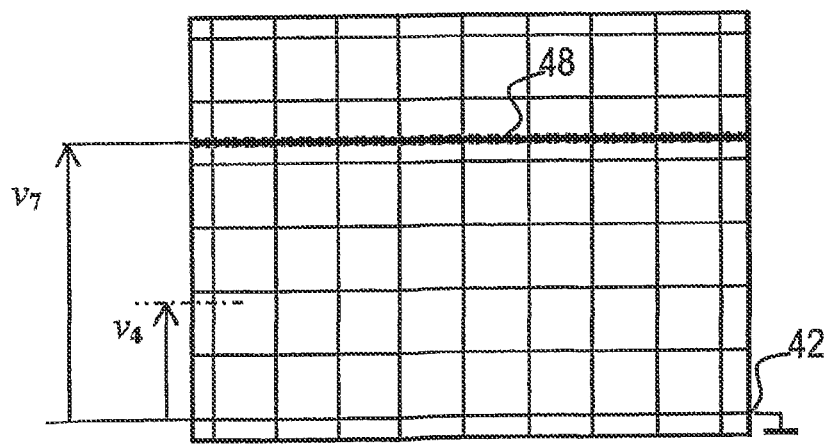
FIG. 9 illustrates the image displayed on the screen of an oscilloscope, corresponding to the signal present at the terminal, when there occur anomalies in the drained currents.

In FIG. 9 there is illustrated the trace on the oscilloscope screen when the excitation current is 5 mA, however the voltage v7 of a signal 48, measured at the terminal 38, is well above the upper limit v4 of then range of tolerance associated with this excitation current. Such condition may be due to an asymmetry in the set of drainage currents of the tomography electrodes 11, such as, for example, the disconnection of one or more electrodes of the set 11. One other possible cause is the connection of another equipment to the patient, such as an electric scalpel, or yet the contact of the patient with an external source of electric power.

Although the invention has been described with relation to a specific embodiment thereof, it should be understood that there may be introduced modifications thereto by technicians skilled in the art, without departing from the spirit and scope of the invention. Thus, for example, FIGS. 1 and 2 indicate the equipment that constitutes the object of the present invention as constituting a unit that is separate from the tomography apparatus 14, however such equipment may be incorporated to the tomography apparatus 14 without prejudice of its functionalities and characteristics.

Therefore, the invention is defined and delimited by the set of claims that follow the instant description.

The invention claimed is:

1. A method of monitoring the current drained by a grounding electrode in electric impedance tomography, the method comprising:
   receiving a ground drainage current from a grounding electrode that is applied along with a set of electrodes of a tomography apparatus to a patient;
   generating a voltage signal from the ground drainage current; and
   comparing a value of the voltage signal with at least one limit value that is dynamic and changes proportional to an intensity of an excitation current applied to the set of electrodes.

2. The method of claim 1, wherein generating the voltage signal comprises amplifying, rectifying, and filtering the ground drainage current to generate a filtered signal.

3. The method of claim 2, wherein generating the voltage signal further comprises digitizing the filtered signal to generate the value of the voltage signal prior to comparing the value with the at least one limit value.

4. The method of claim 1, further comprising detecting that the grounding electrode is disconnected if the value of the voltage signal is substantially equal to zero.

5. The method of claim 1, further comprising detecting an asymmetry in drained currents from the set of the electrodes of the tomography apparatus if the value of the voltage signal is substantially above the at least one limit value.

6. The method of claim 5, wherein the asymmetry is produced by the disconnection of one or more electrodes among the set of electrodes.

7. The method of claim 1, further comprising detecting contact of the patient with an external source of electrical energy if the value of the said voltage signal is substantially above the at least one limit value.

8. The method of claim 7, wherein the external source of electrical energy comprises at least one of an electric scalpel, an electrically conductive body, and a defibrillator.

9. The method of claim 1, further comprising:
   storing a minimum value for a lower limit of a range for the at least one limit value;
   storing a maximum value for an upper limit of the range for the at least one limit value;
   correlating the minimum value with a first excitation current value for the set of electrodes; and
   correlating the maximum value with a second excitation current value for the set of electrodes.

10. The method of claim 9, further comprising adjusting the maximum value and the minimum value defining the range for the at least one limit value responsive to the excitation current being applied to the set of electrodes during operation.

11. The method of claim 1, further comprising positioning the grounding electrode on the patient substantially symmetrically with relation to the set of electrodes applied to the patient.

12. A system for monitoring current drained by a grounding electrode in electric impedance tomography, the system comprising:
   an electric impedance tomography including a set of electrodes and a grounding electrode; and
   an equipment operably coupled with the ground electrode, the equipment configured to:
      generate a voltage signal responsive to the receiving a ground drainage current from the grounding electrode;
      compare a value of the voltage signal with at least one limit value; and
      change the at least one limit value responsive to a change in an intensity of an excitation current applied to the set of electrodes.

13. The system of claim 12, wherein the equipment includes a resistor operably coupled in a path of the ground drainage current drained by the grounding electrode in contact with a patient and a system ground for the electric impedance tomography apparatus.

14. The system of claim 12, wherein the equipment comprises a surge protector operably coupled with the grounding electrode, the surge protector configured to protect the equipment against voltage surges on the grounding electrode.

15. The system of claim 14, wherein the surge protector comprises a pair of diodes connected in counter-parallel fashion between input terminals of the equipment.

16. The system of claim 13, wherein the equipment further comprises an amplifier operably coupled with resistor, the amplifier configured to amplify the voltage signal.

17. The system of claim 12, wherein the equipment and the electric impedance tomography apparatus are incorporated into a common unit.

18. The system of claim 12, wherein the at least one limit value includes a range defined by a minimum limit value and a maximum limit value.

19. The sys of claim 16, wherein the equipment further comprises a demodulator provided with a filter configured to generate a filtered DC signal from the voltage signal derived from the ground drainage current.

20. The system of claim 19, wherein the filter comprises a low-pass filter with a cut-off frequency of 0.5 Hz.

21. An equipment for detecting a condition of an electrical impedance tomography system, comprising:

an input configured to receive a ground drainage current from a grounding electrode of an electric impedance tomography apparatus; and an analysis unit operably coupled with the input, and configured to:

compare a level of a voltage signal derived from the ground drainage current with at least one limit value; and dynamically adjust the at least one limit value responsive to a change in an excitation current applied to a set of electrodes of the electric impedance tomography apparatus.

\* \* \* \* \*

UNITED STATES PATENT AND TRADEMARK OFFICE
CERTIFICATE OF CORRECTION

PATENT NO.         : 8,749,252 B2
APPLICATION NO.    : 12/995350
DATED              : June 10, 2014
INVENTOR(S)        : Maktura Page 1 of 1

It is certified that error appears in the above-identified patent and that said Letters Patent is hereby corrected as shown below:

On the title page:
In ITEM (75) Inventor:        change "São Paulo (BR)" to --São Paulo, SP (BR)--

In the claims:
CLAIM 7,    COLUMN 5,   LINE 66,   change "said voltage" to --voltage--
CLAIM 12,   COLUMN 6,   LINE 26,   change "tomography including" to
                                   --tomography apparatus including--
CLAIM 19,   COLUMN 6,   LINE 60,   change "The sys" to --The system--

Signed and Sealed this
Fifth Day of January, 2016

Michelle K. Lee
*Director of the United States Patent and Trademark Office*